United States Patent
Blakley et al.

(10) Patent No.: US 7,853,014 B2
(45) Date of Patent: *Dec. 14, 2010

(54) RING ARITHMETIC METHOD, SYSTEM, AND APPARATUS

(75) Inventors: George Robert Blakley, Bryan, TX (US); Rajat Datta, Round Rock, TX (US); Oscar Mitchell, Pflugerville, TX (US); Kyle Stein, Round Rock, TX (US)

(73) Assignee: nCipher Corporation Limited, Stoneham, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/712,227

(22) Filed: Feb. 27, 2007

(65) Prior Publication Data

US 2007/0206784 A1    Sep. 6, 2007

(51) Int. Cl.
    *H04L 9/28* (2006.01)
(52) U.S. Cl. .............. 380/28; 380/30; 708/491
(58) Field of Classification Search .......... 380/28, 380/30; 708/491
    See application file for complete search history.

(56) References Cited

U.S. PATENT DOCUMENTS

| | | | |
|---|---|---|---|
| 4,799,149 A | 1/1989 | Wolf | |
| 5,542,061 A | 7/1996 | Omata | |
| 5,699,537 A | 12/1997 | Sharangpani et al. | |
| 5,724,279 A | 3/1998 | Benaloh et al. | |
| 5,764,554 A | 6/1998 | Monier | |
| 5,983,299 A | 11/1999 | Qureshi | |
| 5,987,574 A | 11/1999 | Paluch | |
| 6,088,453 A | 7/2000 | Shimbo | |
| 6,134,244 A | 10/2000 | Van Renesse et al. | |
| 6,141,705 A | 10/2000 | Anand et al. | |
| 6,151,393 A | 11/2000 | Jeong | |
| 6,157,955 A | 12/2000 | Narad et al. | |
| 6,266,771 B1 | 7/2001 | Bellare et al. | |

(Continued)

OTHER PUBLICATIONS

Silverman, Robert D. et al., "Recent Results on Signature Forgery,", Apr. 11, 1999, RSA Labortories Bulletin, pp. 1-5.*

(Continued)

*Primary Examiner*—Michael Pyzocha
(74) *Attorney, Agent, or Firm*—John A. Fortkort; Fortkort & Houston P.C.

(57) ABSTRACT

A data encryption method performed with ring arithmetic operations using a residue number multiplication process wherein a first conversion to a first basis is done using a mixed radix system and a second conversion to a second basis is done using a mixed radix system. In some embodiments, a modulus C is be chosen of the form $2^w-L$, wherein C is a w-bit number and L is a low Hamming weight odd integer less than $2^{(w-1)/2}$. And in some of those embodiments, the residue mod C is calculated via several steps. P is split into 2 w-bit words $H_1$ and $L_1$. $S_1$ is calculated as equal to $L_1+(H_1 2^{x1})+(H_1 2^{x2})+\ldots+(H_1 2^{xk})+H_1$. $S_1$ is split into two w-bit words $H_2$ and $L_2$. $S_2$ is computed as being equal to $L_2+(H_2 2^{x1})+(H_2 2^{x2})+\ldots+(H_2 2^{xk})+H_2$. $S_3$ is computed as being equal to $S_2+(2^{x1}+\ldots+2^{xk}+1)$. And the residue is determined by comparing $S_3$ to $2^w$. If $S_3<2^w$, then the residue equals $S_2$. If $S_3 \geq 2^w$, then the residue equals $S_3-2^w$.

27 Claims, 5 Drawing Sheets

U.S. PATENT DOCUMENTS

| | | | |
|---|---|---|---|
| 6,337,909 B1 * | 1/2002 | Vanstone et al. | 380/28 |
| 6,341,299 B1 | 1/2002 | Romain | |
| 6,718,508 B2 * | 4/2004 | Lodge et al. | 714/780 |
| 7,031,468 B2 * | 4/2006 | Hoffstein et al. | 380/28 |

OTHER PUBLICATIONS

Menezes, A.J. et al., "Handbook of Applied Cryptography" Boca Raton, CRC press, 1997, pp. 611-612.*

Menezes, Alfred at al., "Handbook of Applied Cryptography", CRC Press 1997, pp. 76, 77 and 286.*

Menezes, A.J., et al "Efficient Implementation" from The Handbook of Applied Cryptograph, Boca Raton, CRS Press, 1997, pp. 591-607.

Dimitrov, V. and Cooklev, T., "Two Algorithms for Modular Exponentiation Using Nonstandard Arithmetics" IEICE Trans. Fundamentals, vol. E78-A, No. 1, Jan. 1995, 6 pages.

Koc, C.K. and Hung, C.Y. "Carry-Save Adders for Computing the Product $AB$ Modulo $N$" Electronics Letters, vol. 26, No. 13, Jun. 21, 1990, pp. 899-900.

Freking, W. and Parhi, K.K., "Montgomery Modular Multiplication and Exponentiation in the Residue Number System" Proc. $33^{rd}$ Asilomar Conf. Signals Systems and Computer, Oct. 1999, pp. 1312-1316.

Tenca, A.F. and Koc, C.K., "A Scalable Architecture for Montgomery Multiplication" in: Koc, C.K. and Paar, C. Cryptographic Hardware and Embedded Systems, CHES 99, Lecture Notes in Computer Science, No. 1717. 1998, New York, NY: Springer-Verlag, 1999, 15 pages.

Koc, C.K. and Acra, T., "Montgomery Multiplication in GF $(2^k)$" $3^{rd}$ Annual Workshop on Selected Areas in Cryptography (Aug. 15-16, 1996), pp. 95-106.

Bajard, J.C., et al., "An RNS Montgomery Modular Multiplication Algorithm" IEEE Transactions on Computer, vol. 47, No. 7 (Jul. 1998), pp. 766-776.

Eldridge, S.E., "A Faster Modular Multiplication Algorithm" International Journal of Computer Math, vol. 40 (1991), pp. 63-68.

Bossalaers, A., et al., "Comparison of Three Modular Reduction Functions"; Katholieke Universiteit Leuven, Dept. of Elec. Engineering-ESAT, Heverlee, Belgium; Oct. 25, 1993; pp. 1-10.

Montgomery, P.L., "Modular Multiplication Without Trial Divison" Mathematics of Computation, vol. 44, No. 170 (Apr. 1985), pp. 519-521.

Koc, C.K., et al., "Analyzing and Comparing Montgomery Multiplication Algorithms" IEEE Micro, vol. 16, Issue 3 (Jun. 1996), pp. 26-33.

Kornerup, P., "High-Radix Modular Multiplication for Cryptosystems" Department of Mathematics and Computer Science (1993), pp. 277-283.

Sunar, B. and Koc, C.K., "An Efficient Optimal Normal Basis Type II Multiplier" Brief Contributions, IEEE Transactions on Computers, vol. 50, No. 1 (Jan. 2001), pp. 83-87.

Koc, C.K., "Comments on Residue Arithmetic VLSI Array Architecture for Manipular Pseudo-Inverse Jacobian Computation," Communications, IEEE Transactions on Robotics and Automation, vol. 7, No. 5 (Oct. 1991).

Savas, E. and Koc, C.K., "The Montgomery Modular Inverse-Revisited" IEEE Transactions on Computers, vol. 49, No. 7 (Jul. 2000), pp. 763-766.

Walter, C.D., "Montgomery's Multiplication Technique: How to Make it Smaller and Faster"; Computation Department, UMIST, Manchester UK; (1999); pp. 80-93.

Oh, H. and Moon, J, "Modular Multiplication Method" IEE Proc.-Comput. Digit. Tech., vol. 145, No. 4 (Jul. 1998), pp. 317-318.

Blum, T., "Modular Exponentiation on Reconfigurable Hardware" Master's thesis, ECE Dept., Worcester Polytechnic Institute, Submitted to Faculty Apr. 8, 1999, Published May 1999. Retrieved from the Internet <URL: http://www.wpi.edu/pubs/ETC/Available/etd-090399-090413/unrestricted/blum.pdf>.

Marwedel, P., et al., "Built in Chaining: Introducing Complex Components into Architectural Synthesis" Apr. 1996. Proceedings of the ASP-DAC, 1997 [online]. Retrieved from the Internet <URL: http://eldorado.uni-dortmund.de:8080/FB4/ls12/forhung/1997/aspdac/aspacPFF>; 7 pages.

Tiountchik, A. and Trichina, E., "RSA Acceleration with Field Programmable Gate Arrays"; Institute of Mathematics, Natl. Acad. of Sciences of Belarus, and Advanced Computing Research Centre, Univ of S. Australia (2000); 13 pages.

* cited by examiner

RING ARITHMETIC METHOD, SYSTEM, AND APPARATUS

CROSS-REFERENCE TO RELATED APPLICATIONS

This application claims the benefit of priority from U.S. Utility patent application Ser. No. 10/068,294, now allowed.

This application claims the benefit of the following U.S. Provisional Applications, all of which are hereby incorporated by reference, and the content of which are not necessarily identical to the content of this application:

| Atty. Dkt. # | Serial Number | Title | Filing Date |
|---|---|---|---|
| COMMONLY OWNED AND PREVIOUSLY FILED U.S. PROVISIONAL PATENT APPLICATIONS | | | |
| 501143.000005 | 60/288,015 | Method and Apparatus for Shotgun Multiplication and Exponentiation | May 2, 2001 |
| 501143.000010 | 60/300,957 | Method and Residue Calculation Using Casting Out | Jun. 26, 2001 |
| 501143.000011 | 60/300,955 | Add-Drop Layer 3 Ethernet Ring Switch | Jun. 26, 2001 |
| 501431.000014 | 60/326,266 | Application Specific Information Processing System | Oct. 1, 2001 |
| 501143.000015 | 60/326,252 | Efficient Use of DRAM-Based Devices For Small Discontiguous Memory Accesses | Oct. 1, 2001 |
| 501143.000016 | 60/326,251 | Exponentiation Engine | Oct. 1, 2001 |
| 501143.000017 | 60/326,250 | Method for Squaring | Oct. 1, 2001 |

The current application shares some specification and figures with the following commonly owned and concurrently filed applications, all of which are hereby incorporated by reference:

| Atty. Dkt # | Serial Number | Title | Filing Date |
|---|---|---|---|
| COMMONLY OWNED AND CONCURRENTLY FILED U.S. NONPROVISIONAL PATENT APPLICATIONS | | | |
| 501143.000019 | Not Assigned | Application-Specific Information-Processing Method, System, and Apparatus | Not Assigned |

The benefit of 35 U.S.C. §120 is claimed for all of the above referenced commonly owned applications. The contents of the applications referenced in the tables above are not necessarily identical to the contents of this application. The applications referenced in the tables above are referred to herein as the "Related Applications."

All references cited hereafter are incorporated by reference to the maximum extent allowable by law. To the extent a reference may not be fully incorporated herein, it is incorporated by reference for background purposes and indicative of the knowledge of one of ordinary skill in the art.

BACKGROUND OF THE INVENTION

1. Field of the Invention

The present invention relates generally to ring arithmetic operations and particularly to efficient modular exponentiation of large numbers.

2. Description of Related Art

Modern society has seen information transmission dramatically grow in prevalence, and the importance of information security has likewise grown. Transmitting information over an open network—such as the Internet—involves many security challenges.

The most common Internet protocol for transmitting secured information is Transport Layer Security (TLS), descendent of Secure Sockets Layer (SSL). For clarity because of the protocols' similarities, reference will be made to SSL/TLS throughout this application. To improve speed, SSL/TLS uses symmetric encryption to encrypt much of the transmitted data. But symmetric encryption is vulnerable because communicants must share a private key.

For improved security, SSL/TLS uses the slower asymmetric encryption to share symmetric keys. But every session requires sharing of a new private key because key reuse would substantially increase vulnerability. So in practice new sessions are established frequently, forcing heavy usage of asymmetric encryption.

Some of the principal Internet transactions using this type of security are e-commerce transactions. In a transaction of this type, the consumer transmits identifying information as well as credit-card or other financially sensitive data to a vendor. The amount of data that must be encrypted to complete the transaction is very small, typically less than twenty lines of text. The time spent by a server encrypting this data is insignificant compared with the time necessary to encrypt and decrypt the symmetric key in the asymmetric key-exchange portion of the transaction. Because each session requires a new key, which must be encrypted and then decrypted using the slow asymmetric encryption process, whenever a significant number of sessions are established, the majority of server resources may be dedicated to the key exchange protocol.

BRIEF SUMMARY OF THE INVENTION

A preferred embodiment is a data encryption method performed with ring arithmetic operations using a residue number multiplication process wherein a first conversion to a first basis is done using a mixed radix system and a second conversion to a second basis is done using a mixed radix system. In some embodiments, a modulus C is be chosen of the form $2^w - L$, wherein C is a w-bit number and L is a low Hamming weight odd integer less than $2^{(w-1)/2}$. And in some of those embodiments, the residue mod C is calculated via several steps. P is split into 2 w-bit words $H_1$ and $L_1$. $S_1$ is calculated as equal to $L_1 + (H_1 2^{x_1}) + (H_1 2^{x_2}) + \ldots + (H_1 2^{x_k}) + H_1$. $S_1$ is split into two w-bit words $H_2$ and $L_2$. $S_2$ is computed as being equal to $L_2 + (H_2 2^{x_1}) + (H_2 2^{x_2}) + \ldots + (H_2 2^{x_k}) + H_2$. $S_3$ is computed as being equal to $S_2 + (2^{x_1} + \ldots + 2^{x_k} + 1)$. And the residue is determined by comparing $S_3$ to $2^w$. If $S_3 < 2^w$, then the residue equals $S_2$. If $S_3 \geq 2^w$, then the residue equals $S_3 - 2^w$.

Further features and advantages of the invention will become apparent from the following detailed description and accompanying drawings.

BRIEF DESCRIPTION OF THE DRAWINGS

The following drawings form part of the present specification and are included to further demonstrate certain aspects of the present invention. The figures are not necessarily drawn to scale. The invention may be better understood by reference to one or more of these drawings in combination with the detailed description of specific embodiments presented herein.

DETAILED DESCRIPTION OF PREFERRED EMBODIMENTS

Figure 1A:
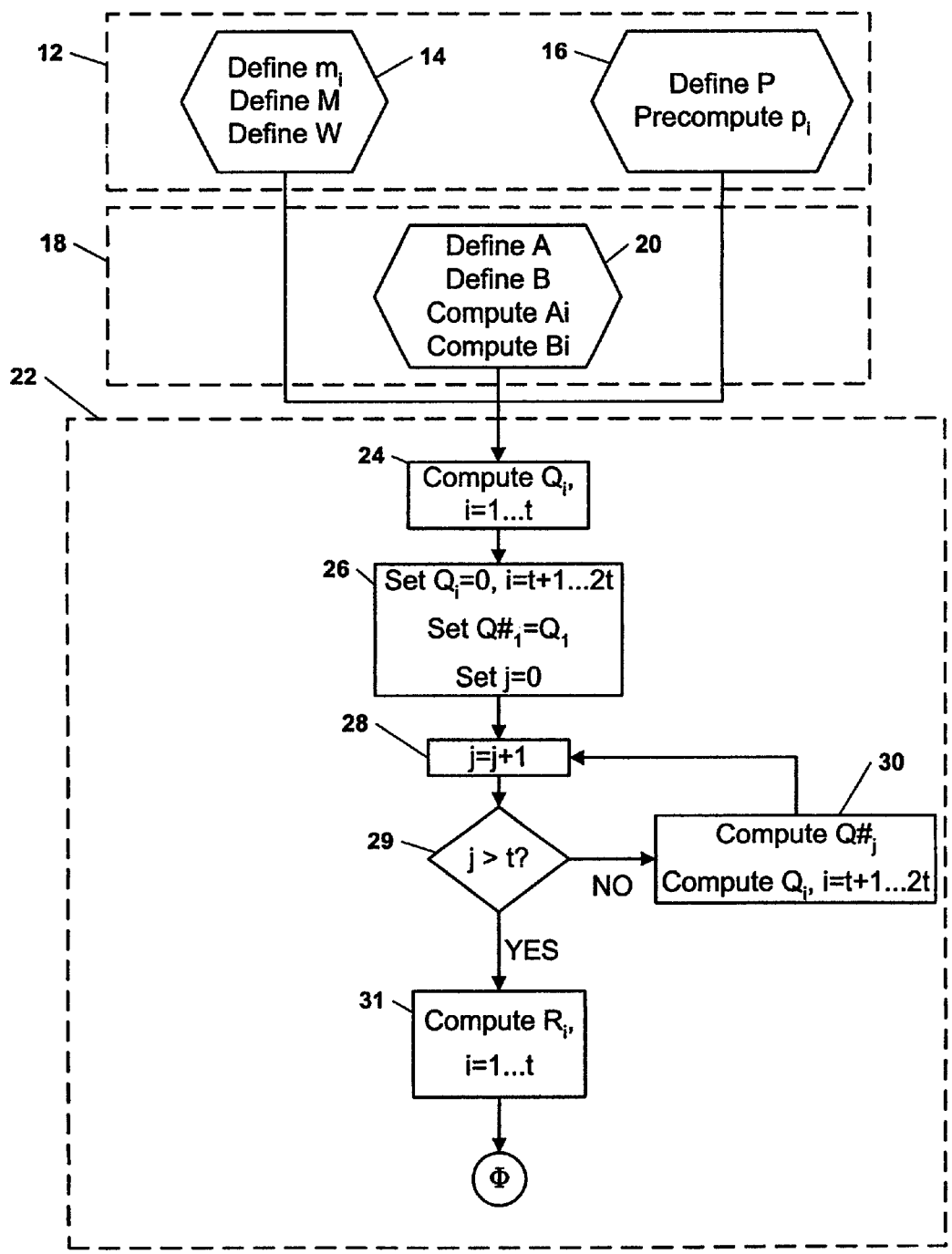
FIGS. 1A and 1B show a flowchart of a shotgun multiplication process, in accordance with an embodiment of the present invention.

Rivest Shamir Adleman (RSA) is one of the most common types of public key cryptography and is used for key exchanges in SSL/TLS. RSA bases its security claims on the difficulty of factoring large numbers. The public and private keys are functions of a pair of large prime numbers. Cryptanalyzing the encrypted message using only the public key could be of comparable difficulty to factoring the product of two large primes.

The two large prime numbers p and q are used to generate the members of a key pair. The product is computed: N=pq. An encryption key e is chosen such that e and (p−1)(q−1) are relatively prime. The decryption key $d = e^{-1} (\mod (p-1)(q-1))$ is computed from e using the extended Euclidean algorithm. For a plaintext message S, a ciphertext message A is created by computing $A = S^e \mod N$. Then computing $S = A^d \mod N$ decrypts ciphertext A, giving plaintext S.

The Residue Number System (RNS) can be used to improve efficiency. Given a list of pair-wise relatively prime moduli $m_1, m_2, \ldots m_k$, called an RNS basis, the RNS representation of a number X with respect to this RNS basis is the k-tuple $(x_1, x_2, \ldots x_k)$ where $x_i = X \mod m_i$. The importance of the residue number system to numerical processes is that the operations of addition, subtraction, and multiplication modulo M (where M is the product of the moduli) can be performed without the use of carry operations between the moduli. In other words, each coordinate in the k-tuple can be operated on independently and in parallel.

The Chinese Remainder Theorem (CRT) of elementary number theory states that given an RNS basis there is a one-to-one correspondence between the RNS k-tuples and the residues modulo M, where M is the product of the moduli of the basis.

CRT may be stated as follows. For a given list of positive integers $m_1, m_2, \ldots m_k$ such that the greatest common divisor (gcd) of any pair $m_i, m_j$ ($i \neq j$) is 1, then for any list of non-negative integers $r_1, r_2, \ldots r_k$ such that $r_i < m_i (i=1, k)$, there exists a unique integer X such that $X (\mod m_i) = r_i (i=1, k)$ and $X < m_1 m_2 \ldots m_k$, and conversely, each such X determines a unique such list of $r_i$.

In RSA decryption it is necessary to calculate $S = A^d \mod N$. Now, N=pq and gcd (p,q)=1 since p and q are both prime. So CRT uniquely determines S mod N by the pair (S mod p, S mod q).

$$S \mod p = (A^d \mod N) \mod p$$
$$= A^d \mod p$$
$$= a^d \mod p$$
$$= a^{u(p-1)+v} \mod p$$
$$= (a^{u(p-1)} \mod p)(a^v \mod p) \mod p$$
$$= ((a^{(p-1)})^u \mod p)(a^v \mod p) \mod p$$
$$= ((1)^u \mod p)(a^v \mod p) \mod p$$
$$= a^v \mod p$$

Since N is a multiple of p where $a = A \mod p$ for some integer u, and for $v = d \mod(p-1)$ by Euler's theorem Similarly, $S \mod q = b^h \mod q$, where $b = A \mod q$, and $h = d \mod(q-1)$.

Consider the value $U = ((sp-sq) g \mod p) q + sq$ where $sq = S \mod p$, $sq = S \mod q$, and g is such that $g q = 1 \mod p$. $U \leq (p-1)q + q - 1 < pq = N$. Also $U \mod q = sq = S \mod q$ and $$U \mod p = (((sp - sq)g \mod p)q + sq) \mod p$$
$$= ((sp - sq)gq \mod p + sq) \mod p$$
$$= ((sq - sq)1 \mod p + sq) \mod p$$
$$= sp \mod p$$
$$= S \mod p$$

So by the CRT, U=S mod N.
Hence, in order to calculate $S = A^d \mod N$
1) Compute:
   a) $sp = (A \mod p)^{d \mod(p-1)} \mod p$
   b) $sq = (A \mod q)^{d \mod(q-1)} \mod q$
2) Find g with $0 < g < p$ and $gq = 1 \mod p$
3) Compute $S = ((sp-sq) g \mod p) q + sq$ Thus the problem of calculating $S = A^d \mod N$ where A, d and N are 2n bit numbers, is reduced to one of calculating two values sp and sq which are n bit numbers. This represents a considerable saving in computation time.

The Mixed Radix System (MRS) expression of a given integer X modulo M (as above) is $$X = x\#_1 + x\#_2 m_1 + x\#_3 m_1 m_2 + x\#_k m_1 m_2 \ldots m_{k-1} \quad 0 \leq x\#_i < m_i$$

The $x\#_i$ in the above are called the MRS digits of X. They are unique and can be calculated from the RNS residues $x_1, x_2 \ldots x_k$ ($x_i = X \mod m_i$) by the following recursion:

$$x\#_1 = x_1$$
$$x\#_2 = (x_2 - x\#_1) m_1^{-1} \mod m_2$$
$$x\#_3 = ((x_3 - x\#_1) m_1^{-1} - x\#_2) m_2^{-1} \mod m_3$$
$$\ldots$$
$$x\#_j = (\ldots ((x_j - x\#_1) m_1^{-1} - x\#_2) m_2^{-1} - \ldots - x\#_{j-1}) m_{j-1}^{-1} \mod m_j$$

The Montgomery Modular Multiplication (MMM) facilitates repetitive modular reduction operations, mod N, where N is an odd integer constant. Public key cryptography depends heavily on arithmetic operations modulo a multiple-precision odd integer. So the performance of a public key cryptosystem depends heavily on the speed with which it executes those operations. Multiplications and divisions have particularly large influences on processing time. The Montgomery method particularly facilitates repeatedly executing multiplications. The Montgomery method is a method for computing multiple-precision modular multiplication with a processing cost of about two multiple-precision multiplications. Multiple-precision modular reduction usually has a poor performance compared with multiple-precision multiplication, so the Montgomery method can significantly improve performance.

Suppose two numbers are to be multiplied. First, they are each transformed into Montgomery space by taking mod p of each. Then the Montgomery multiplication is carried out, and its result is inversely transformed out of Montgomery space. The transformation and inverse transformation each have a processing load of about one multiple-precision multiplication. Consequently, modular exponentiation suffers lower overhead due to the Montgomery conversion and the inverse Montgomery conversion because it carries out modular multiplications repeatedly and therefore it can be realized by a fast implementation. The Montgomery method can benefit many public key algorithms, including RSA, that use modular exponentiation, $S = A^d \mod N$, as their basic operation. But the Montgomery method will not necessarily lead to efficient implementation if only some multiplications are required due to transform and inverse transform overhead.

Various MMM methods are known. See, for example, Peter L. Montgomery, "Modular Multiplication Without Trial Division", Mathematics of Computations, vol. 44, no. 170, pp. 519-521, April 1985; Stephen P. Dussé and Burton S. Kaliski, Jr., "A Cryptographic Library for the Motorola DSP 56000", Advances in Cryptography, Proc Eurocrypt'90, Lecture Notes In Computer Science no. 473, pp. 230-244, Springer-Verlag, 1990; and the methods of U.S. Pat. No. 4,514,592 to Miyaguchi, U.S. Pat. No. 5,101,431, to Even, U.S. Pat. No. 5,321,752 to Iwamura, U.S. Pat. No. 5,448,639, to Arazi, and U.S. Pat. No. 5,513,133 to Gressel.

Shotgun Multiplication

Figure 1B:
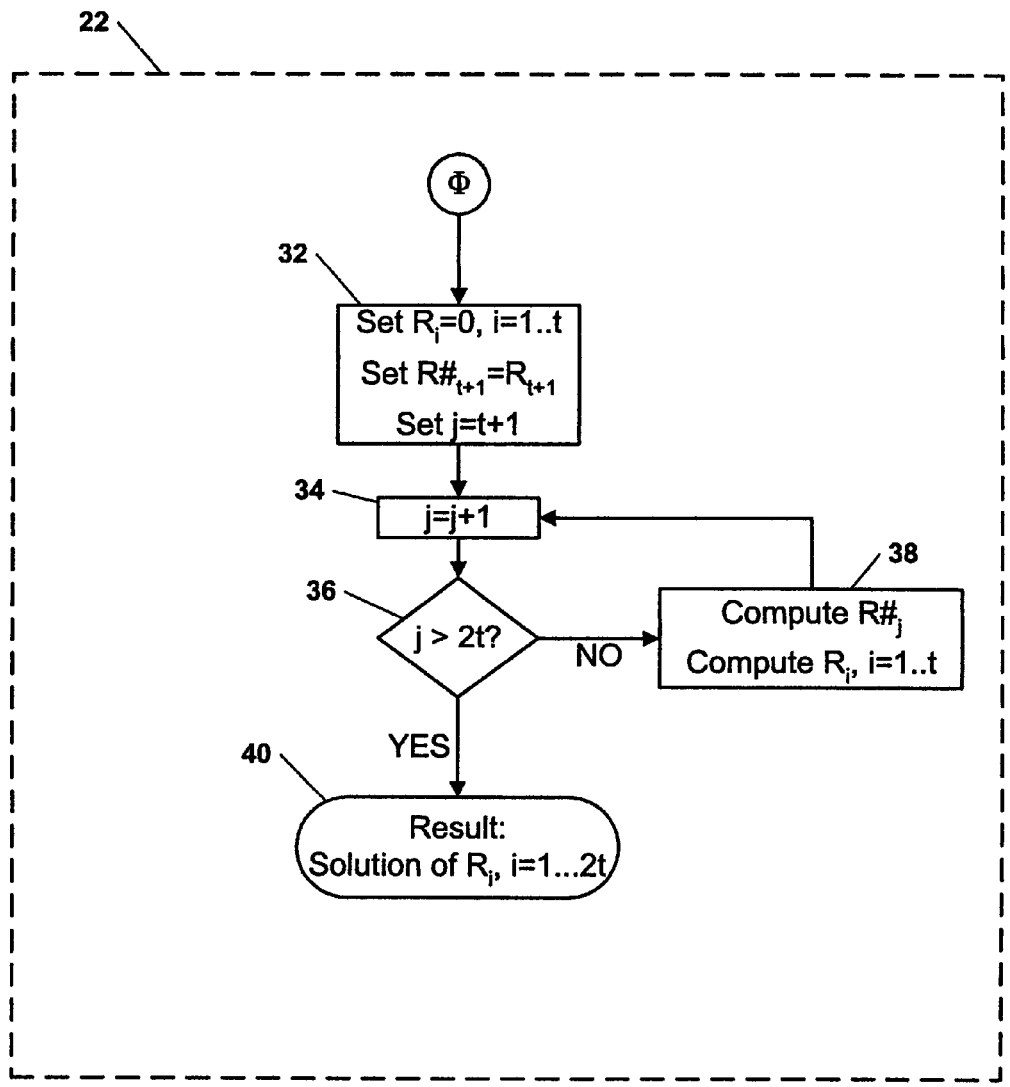

FIGS. 1A and 1B depict a shotgun multiplication process. The processing occurs in parallel mathematically independent units. In a precomputation phase 12 $m_i$, M, and W are defined 14. The $m_i$ are k-bit moduli ($m_1, m_2, \ldots m_{2t}$), where the moduli $m_i$ are pairwise mutually prime and $t \geq (n+1)/k$, where n is the bit length of the numbers being multiplied. M is defined as the product of the first t moduli: $M = m_1 m_2 \ldots m_t$. W is defined as the product of the second t moduli: $W = m_{t+1} m_{t+2} \ldots m_{2t}$. By k-bit moduli, we mean $2^{k-1} \leq m_i < 2^k$. This means that $M > 2^{n+1}$ and $W > 2^{n+1}$. Additionally, $m_i^{-1} \mod m_j$ are calculated for $i,j = 1 \ldots 2t$ with $i \neq j$.

During the precomputation phase 12, $p_i$ is also defined 16 such that p is an n-bit number and $p_i = p \mod m_i$ for $i = t+1 \ldots 2t$. Additionally, $p^{-1}_i$ is calculated for $i = 1 \ldots t$. Note that p must be relatively prime to M and W, and p is usually prime.

During a setup phase 18, $A_i$ and $B_i$ are defined 20 for n-bit numbers A and B. To multiply A and B modulo p, the numbers are rendered in RNS notation so that $A_i = A \mod m_i$ and $B_i = B \mod m_i$ and $p_i = p \mod m_i$ for $i = 1 \ldots 2t$ in both RNS bases.

The rest of the shotgun multiplication process depicted in FIGS. 1A and 1B all falls within the body phase 22.

It takes as parameters arguments A and B from 20 and modulus p in Residue Number System (RNS) notation from 16 for a first RNS basis (moduli $m_1, \ldots m_t$) and for a second RNS basis (moduli $m_{t+1}, \ldots m_{2t}$) from 14. Its output 40 is $R = ABM^{-1} \mod p$ expressed in the both the first and the second RNS bases. This allows the outputs 40 to be used as inputs in subsequent multiplications. As in 14, M is the product of the moduli in the first RNS basis. And as also in 14, W is the product of the moduli in the second RNS basis.

Shotgun multiplication facilitates the necessary computations by working in the first basis where computing a multiple of M is easy and then converting to the second basis where division by M is easy.

This basis conversion is done by means of deriving the Mixed Radix System (MRS) digits of a number in one basis, and computing the corresponding sum in the other basis. This technique lends itself to parallel, computations. In general the process performs the following sequence of steps:

Step 1: In the first basis compute Q mod M such that $AB + Qp = RM$ for some integral value R. This is equivalent to the computation:

$$AB + Qp = 0 \mod M$$

or $$Q = -ABp^{-1} \mod M.$$

Step 2: Convert Q to the second basis, Q mod W.
Step 3: Compute R in the second basis, R mod W.

$$R = (AB + Qp)M^{-1} \mod W$$

Note that $M^{-1}$ exists in the second basis (mod W) but not in the first where M mod M=0. Also note that $$R \mod p = (AB + Qp)M^{-1} \mod p$$
$$= ABM^{-1} + QM^{-1}p \mod p$$
$$= ABM^{-1} \mod p,$$

which is the answer we are looking for.

Step 4: Convert R back to the first basis so that it can be used as input to the next multiplication.

The strength of this process lies in the fact that there are many operands that do not depend on A or B, depending only on p or the $m_i$. These operands can be precomputed one time for many different p in the same size range and stored for repeated reference.

The set of $Q_i$'s is the set of RNS values corresponding to $Q = -ABp^{-1} \mod M$. The RNS values $Q_i$ are computed as $Q_i = -A_i B_i p^{-1}_i \mod m_i$ for $i = 1 \ldots t$ in 24. Note that the $Q_i$'s are computed without reference to Q, and $p^{-1} \mod M$ is a precomputed value as described above.

In Steps 26-30, Q is then converted from the RNS basis ($m_1, m_2, \ldots m_t$) to RNS basis ($m_{t+1}, m_{t+2}, \ldots m_{2t}$) by computing the MRS expansion $Q = Q\#_1 + Q\#_2 m_1 + Q\#_3 m_1 m_2 + \ldots + Q\#_t m_1 m_2 \ldots m_{t-1}$. To perform this expansion, $Q_i = 0$ for $i = t+1 \ldots 2t$. $Q\#_1 = Q_1$. Counter j is set to zero.

In step 28, the counter is incremented: $j = j+1$.

In step 29, j is compared to t. If j is less than or equal to t, then $Q\#_j$ is computed in 30:

$$Q\#_j = (\ldots ((Q_j - Q\#_1) m_1^{-1} - Q\#_2) m_2^{-1} - \ldots Q\#_{j-1}) m_{j-1}^{-1},$$
and the second basis values of $Q_i$ are updated:

$$Q_i = Q_j + Q\#_j (m_1 m_2 \ldots m_{j-1}) \text{ for } i = t+1, \ldots 2t.$$

Then the process returns to step 28, where the counter is again incremented, etc.

But if, in step 29, j is greater than t, the conversion of Q to the second basis is complete, i.e. $Q_i = Q \bmod m_i$, for $i = t+1 \ldots 2t$.

Then in 31 the set of $R_i$'s is the set of RNS values corresponding to $R \bmod p = ABM^{-1} \bmod p$. The RNS values $R_i$ are computed as $R_i = (A_i B_i + Q_i p_i)(M^{-1}) \bmod m_i$ for $i = t+1 \ldots 2t$. Note that the $R_i$'s are computed without reference to R. Also note that $(M^{-1}) \bmod m_i$ is also a precomputed value.

Because this multiplication process is used recursively when doing exponential operations, R is converted from the second RNS basis $(m_{t+1}, m_{t+2}, \ldots m_{2t})$ to the first RNS basis $(m_1, m_2, \ldots m_t)$ by computing the MRS expansion $R = R\#_{t+1} + R\#_{t+2} m_{t+1} + R\#_{t+3} m_{t+1} m_{t+2} + \ldots + R\#_{2t} m_{t+1} m_{t+2} \ldots m_{2t-1}$.

Then in 32, $R_i = 0$ for $i = 1 \ldots t$. $R\#_{t+1} = R_{t+1}$. Counter j is set to $t+1$.

In step 34, the counter is incremented: $j = j+1$.

In step 36, j is compared to 2t. If j is less than or equal to 2t, then $R\#_j$ is computed in step 38:

$$R\#_j = (\ldots ((R_j - R\#_{t+1}) m_{t+1}^{-1} - R\#_{t+2}) m_{t+2}^{-1} - \ldots R\#_{j-1})^{-1}) m_{j-1}^{-1} \bmod m_j$$

$$R_i = R_i + R\#_j (m_{t+1} m_{t+2} \ldots m_{2t}) \text{ for } i = 1 \ldots t.$$

Then the process loops back to step 34, where the counter is again incremented and so on.

If, in step 36, j is greater than 2t, the result 40 is obtained:

$$R_i = (ABM^{-1} \bmod p) \bmod m_i, \text{ for } i = 1 \ldots 2t.$$

If another iteration of the shotgun multiplication process of FIGS. 1A and 1B follows, then this $R_i$ would go into the subsequent shotgun multiplication iteration. The subsequent iteration would include body 22, with the $R_i$ being used in place of $A_i$.

In an embodiment, shotgun multiplication is best described as follows:

Shotgun ring operations for cryptographic purposes, or for other technical, commercial or governmental purposes, are high-speed ways of adding, negating, subtracting and multiplying numbers.

The Chinese Remainder Theorem gives a constructive definition of a useful ring isomorphism between two important commutative rings with unity, the ring Z/mZ of integers modulo m, and a related product ring P, the product being over factor rings indexed by the members of an appropriate index set of pairwise relatively prime divisors of m.

Shotgun arithmetic proceeds by performing a succession of operations involving members a, b, c, . . . of the ring Z/mZ, as follows:

Step 1: "Shatter" member a into many "shards", one belonging to each factor ring F of the product ring P. In other words, use the CRT to "encode" the integer a into the integer a mod f if the factor ring F is equal to Z/fZ. Similarly shatter members b, c, . . . .

Step 2(a): Appropriately operate on the F-shards of the members of Z/mZ involved in the first operation. Do this separately, for each F, so as to accumulate a family of result-shards corresponding to the first operation of the desired succession of operations, one result-shard belonging to each factor ring F.

Step 2(b): Remain at the shard level, and do the next appropriate operation within each factor ring F, producing a next family of result-shards, one for each F.

Step 2(c): And again. And again . . . . Never departing from the shard level, which is to say from operations within each single factor ring F.

Step 3: When the desired succession of ring operations on numbers belonging to the ring Z/mZ has been mimicked by an actual succession of corresponding families of F ring operations on shard-level in the separate factor rings F, it is necessary to "unshatter" the family of final shard-results, one in each factor ring F. In accordance with the CRT, this is done by the Euclidean Algorithm methodology.

Sliding Window S-Ary Exponentiation

Figure 2:
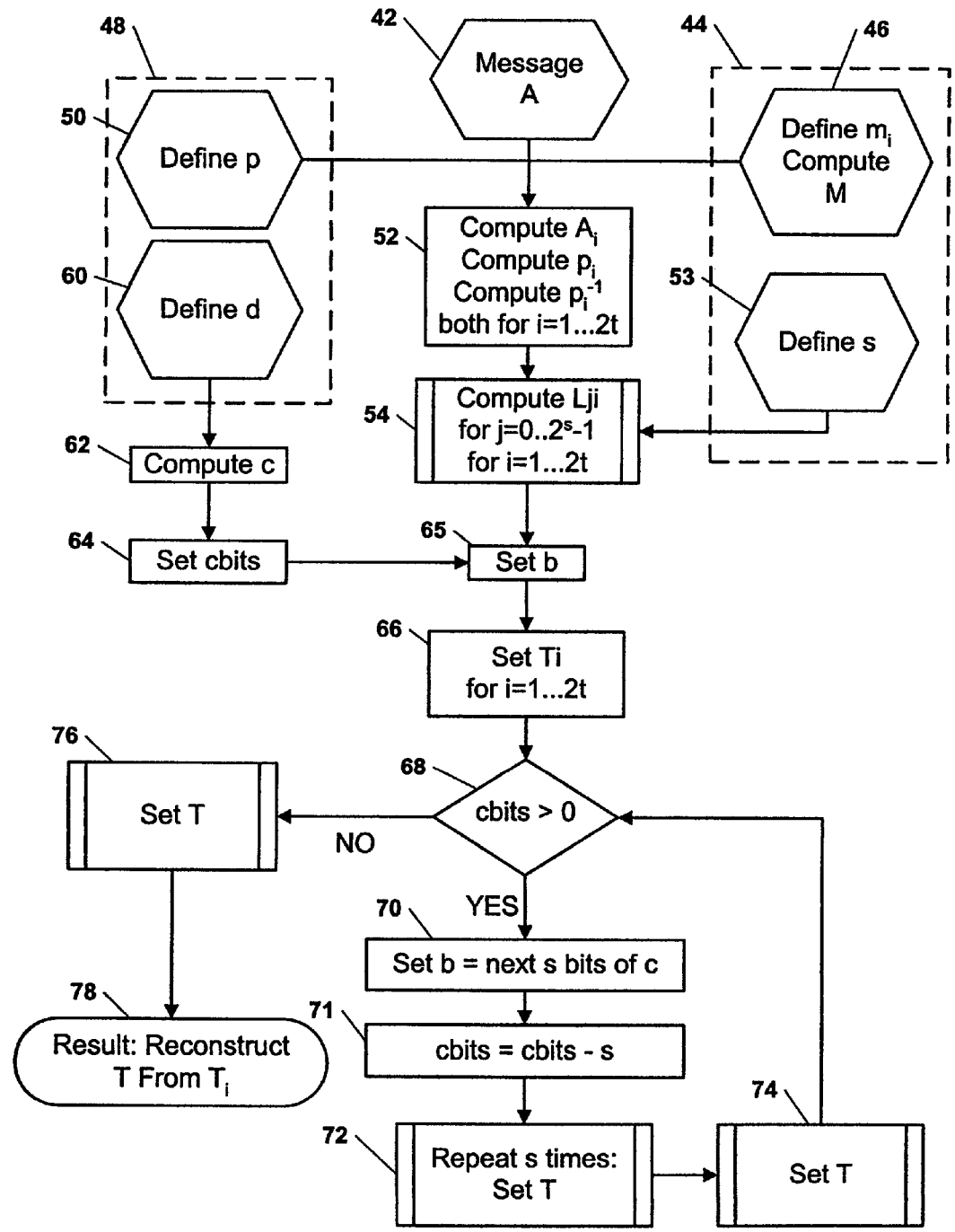
FIG. 2 shows a flowchart of a sliding window s-ary exponentiation, in accordance with an embodiment of the present invention.

FIG. 2 depicts a method for exponentiation mod prime p through repeated squarings and multiplications. This flow introduces data, specifically the $m_i$ moduli that are essential in the shotgun multiplication process used in each of the demarcated boxes. A shotgun multiplication process is detailed in FIGS. 1A and 1B. The exponentiation method ultimately calculates $A^d \bmod p$.

In 42, message A has a bit length of n bits. The message A could be any number or other information represented in a digital format. Method parameters are shown in 44. In 46, k-bit moduli $(m_1, m_2, \ldots m_{2t})$ are chosen, where the moduli $m_i$ are pairwise relatively prime and $t \geq (n+1)/k$. And also in 46, M is defined as the product of the first t moduli: $M = m_1 m_2 \ldots m_t$.

As a first part of a key 48 a modulus p is input 50, where p is an n-bit prime modulus.

In 52 the message A and modulus p are rendered in RNS notation so that $A_i = A \bmod m_i$ and $p_i = p \bmod m_i$ for $i = 1 \ldots 2t$. The modular inverse of p is also calculated $p^{-1}_i = p^{-1} \bmod m_i$ for $i = 1 \ldots 2t$.

The second parameter 44 is a sliding window width s shown in 53. The sliding window width s is chosen (and fixed for a given implementation) by weighing the cost of storage $\sim t(k)(2^s)$ bits against the cost of computation $\sim 2^s + n + n/s$ multiplications. Sliding window widths in the range of 1 to 6 would be common.

Using the shotgun multiplication process in 54, $L_{ji}$ is computed such that $L_{ji} = (A^j M^{j-1} \bmod p) \bmod m_i$, for $j = 0 \ldots 2^s - 1$ and $i = 1 \ldots 2t$. And:

$$L_0 =$$

$$L_1 = A$$

$$L_2 = SG(L_1, A) = L_1 A M^{-1}$$

$$\ldots$$

$$L_j = SG(L_{j-1}, A) = L_{j-1}(AM^{-1}) = A^{j-1} M^{j-2}(AM^{-1}) = A^j M^{j-1}$$

where SG( ) denotes shotgun multiplication.

As a second part of key 48, input 60 is a 2n-bit exponent d. In 62 a variable c is set equal to $d \bmod (p-1)$. And in 64 variable pointer cbits is set equal to the number of bits in c.

In step 65, a variable b is set equal to the first s bits of c. In step 66, a variable $T_i$ is set equal to $L_{bi}$.

The determination 68 is then made of whether there are more bits in c to process. If yes, then in 70 b = s bits of c, starting at cbits. Then in 71, cbits = cbits - s.

The shotgun multiplication process is repeated s times in 72, each time setting $T = T^2 M^{-1} \bmod p$, where $T_i = T \bmod m_i$, wherein T is realized in RNS notation, $T_i = T \bmod m_i$, $i = 1 \ldots 2t$. The shotgun multiplication process is then used in 74 to set $T = TL_b M^{-1} \bmod p$, wherein T is realized in RNS notation, $T_i = T \bmod m_i$, $i = 1 \ldots 2t$.

The method then loops to make determination 68 again and so on.

If the determination 68 is no, the shotgun multiplication process is used in 76 to set $T = TM^{delta(c)} \bmod p$, wherein T is realized in RNS notation, $T_i = T \bmod m_i$, $i = 1 \ldots 2t$, and wherein delta(c) is the number of powers of $M^{-1}$ accumulated in the shotgun multiplications, including squarings, in the 68-70-72-74 loop. Because delta(c) is solely determined by c, it can be precomputed.

Finally, in 78 T is recovered from $T_i$ using the Chinese Remainder Theorem (CRT). In fact, $T = A^d \mod p$.

Exponentiation Mod pq Using CRT

Figure 3:
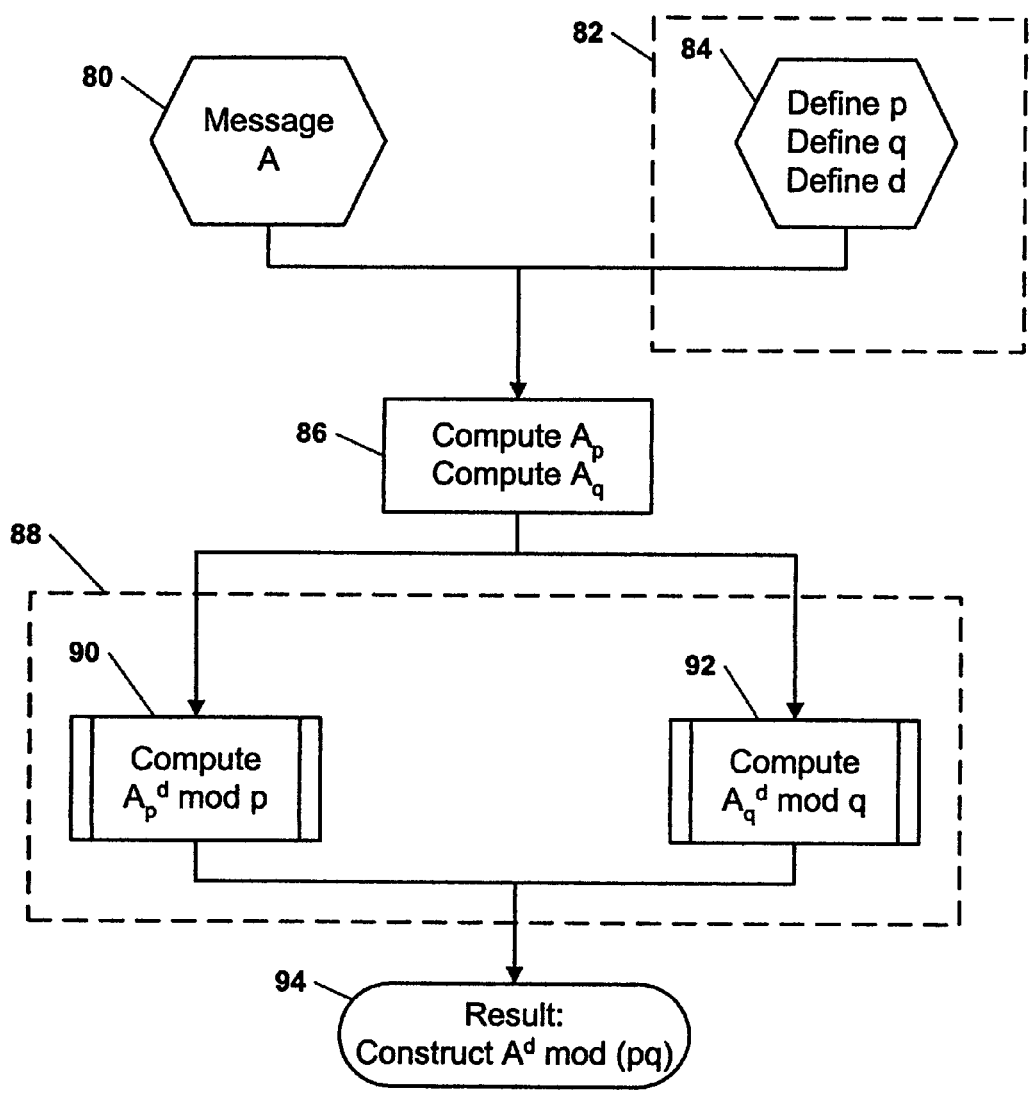
FIG. 3 shows a flowchart of an exponentiation mod pq using Chinese Remainder Theorem, in accordance with an embodiment of the present invention.

FIG. 3 depicts a method of using CRT to break a 2n-bit exponentiation into two n-bit exponentiations (which in practice are each one eighth as expensive.) It requires that the prime factors p and q of the modulus N be known. It employs the sliding window exponentiation process described in the second flow.

The process begins in 80 with a 2n-bit message A. Then a key 82 is chosen 84. The components 84 of key 82 include n-bit prime numbers p and q, and a 2n-bit exponent d.

In step 86, $A_p$ and $A_q$ are computed:

$$A_p = A \mod p$$

$$A_q = A \mod q$$

Then the sliding window exponentiation process is used in 88 to compute $A_p^d \mod p$ in 90 and $A_q^d \mod q$ in 92.

Finally in 94, $A^d \mod(pq)$ is constructed using CRT.

Castout

The shotgun multiplication method can be used more efficiently by choosing the bases $(m_1, \ldots m_{2t})$ in ways that make the modular calculations simpler. A w-bit number C is a "castout modulus" if it is of the form $2^w - L$, where L is a low Hamming weight odd integer less than $2^{(w-3)/2}$, i.e., $C = 2^w - 2^{x1} - 2^{x2} - \ldots - 2^{xk} - 1$, where $(w-3)/2 > x_1 > x_2 > \ldots > x_k > 0$ and k is much less than w. The "castout order" of C is defined to be one less than the Hamming weight of L.

The residue of a modulo $<2^{2w}$ a w-bit castout modulus can be found using only $2k+3$ additions, $2k$ multiplications by $2^x$ (shifts) and a single bit comparison, where k is the castout order of the modulus.

Figure 4:
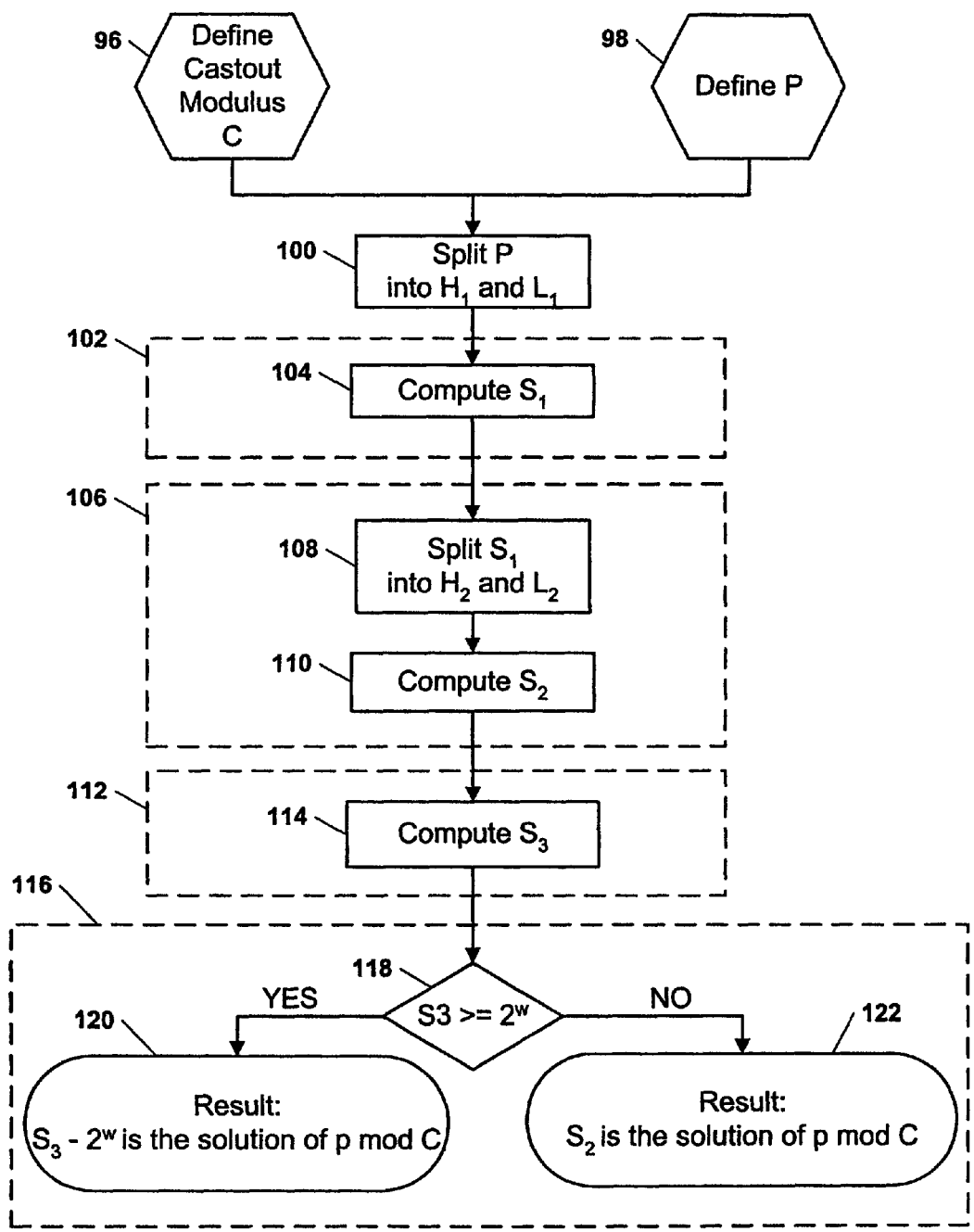
FIG. 4 shows a flowchart of a castout process, in accordance with an embodiment of the present invention.

FIG. 4 illustrates the castout process.

Let C be a w-bit castout modulus of order k in 96 such that $$C = 2^w - 2^{x1} - 2^{x2} - \ldots - 2^{xk} - 1.$$

And let P be a number $<2^{2w}$ in 98.

Then in 100, consider P as two w-bit words $H_1$ and $L_1$ wherein $$P = 2^w H_1 + L_1, \text{ with } L_1 < 2^w \text{ and } H_1 < 2^w.$$

Step 1: This step 102 computes $S_1$ 104:

$$S_1 = L_1 + (H_1 2^{x1}) + (H_1 2^{x2}) + \ldots + (H_1 2^{xk}) + H_1$$

Step 2: This step 106 splits $S_1$ 108 and computes $S_2$ 110:
Consider $S_1$ as two w-bit words $H_2$ and $L_2$
Such that $S_1 = 2^w H_2 + L_2$ Compute $S_2 = L_2 + (H_2 2^{x1}) + (H_2 2^{x2}) + \ldots + (H_2 2^{xk}) + H_2$ Step 3: This step 112 computes $S_3$ 114:

Compute $S_3 = S_2 + (2^{x1} + \ldots + 2^{xk} + 1)$

Step 4: This step 116 compares $S_3 \geq 2^w$ 118, leading to either $S_3 - 2^w$ 120 or $S_2$ 122:
If $S_3 \geq 2^w$ (the w+1 bit of $S_3$ is 1) then output $S_3 - 2^w$ (the low w bits of $S_3$), otherwise output $S_2$ Justification:

$$P = 2^w H_1 + L_1$$
$$= H_1^*(C + 2^{x1} + \ldots + 2^{xk} + 1) + L_1$$
$$= L_1 + 2^{x1} H_1 + \ldots + 2^{xk} H_1 + H_1 + H_1 C$$
$$= S_1 + H_1 C,$$

so $S_1 \equiv P \mod C$.

Also, $S_1 = L_1 + (2^{x1} + \ldots + 2^{xk} + 1) H_1 < L_1 + 2(2^{x1}) H_1 < 2^w +$
$$2(2^{(w-3)/2}) 2^w$$
$$= 2^w (2^{(w-1)/2} + 1) < 2^w (2^{(w+1)/2})$$
$$= 2^{(3w+1)/2}$$

$S_1 = 2^w H_2 + L_2$, with $L_2 < 2^w$ and $H_2 < 2^{(w+1)/2}$ $$S_1 = 2^w H_2 + L_2$$
$$= H_2 (C + 2^{x1} + \ldots + 2^{xk} + 1) + L_2$$
$$= L_2 + 2^{x1} H_2 + \ldots + 2^{xk} H_2 + H_2 + H_2 C$$
$$= S_2 + H_2 C,$$

so, $S_2 \equiv S_1 \equiv P \mod C$.

Also, $S_2 = L_2 + (2^{x1} + \ldots + 2^{xk} + 1) H_2 < L_2 + 2(2^{x1} H_2) < 2^w +$
$$2(2^{(w-3)/2}) 2^{(w+1)/2}$$
$$= 2^w + 2^{(2w-1)/2} < 2^{w+1} < 2C$$

If $S_3 \geq 2^w$, then $$S_3 - 2^w = S_2 + (2^{x1} + \ldots + 2^{xk} + 1) - 2^w$$
$$= S_2 - C$$
$$\equiv P \mod C, \text{ and}$$

and $$S_3 = S_2 - C < 2C - C$$
$$= C$$

Otherwise, if $S_3 < 2^w$,
then $S_2 + (2^{x1} + \ldots + 2^{xk} + 1) < 2^w$, so $S_2 < C$ And $S_2 \equiv P \mod C$ as shown above Computation of $S_1$ and $S_2$ take $k+1$ additions and k shifts each. Computation of $S_3$ takes one addition, and the decision on what to output is a one-bit comparison. These total $2k+3$ additions, $2k$ shifts and one one-bit comparison.

In order to find the residue, modulo C, therefore, it is only necessary to calculate 104 $S_1$ using Step 1 in 102, calculate 110 $S_2$ using Step 2 in 106, calculate 114 $S_3$ using Step 3 in 112 and perform a one-bit compare 118 of $S_3$ against $2^w$ and output either $S_3 - 2^w$ in 120 or $S_2$ in 122, depending on the result of the compare 118.

The residue calculated in this fashion can be used in a variety of processes, particularly to perform large number exponentiation in public key cryptography.

Generalization of Castout

Some embodiments select castout moduli from two sets of numbers: (1) big and heavy numbers or (2) little and light numbers.

A definition of a "w-big" number used by some embodiments is: a w-big number is a number less than $2^w$ but close to $2^w$. A definition of a "w-heavy" number used by some embodiments is: a w-heavy number is a number less than $2^w$ and with Hamming weight close to w.

A definition of a "w-little" number used by some embodiments is: a w-little number is a number greater than $2^w$ but close to $2^w$. A definition of a "w-light" number used by some embodiments is: a w-light number is a number greater than $2^w$ and with Hamming weight close to 1.

Another definition of a "w-big" number used by some embodiments is: a w-big number is greater than $>2^w-2^{gw}$ where g is a number less than 1. That is, the upper w(1−g) bits of the w-big number are 1 when the w-big number is written in binary notation. For example, one embodiment defines a w-big w-heavy number by g=½ and |x−w|≦6.

Some embodiments achieve computational advantages by using a castout modulus that is both w-big and w-heavy. Some embodiments achieve computational advantages by using a castout modulus that is both w-little and w-light. The detailed computational discussion in this application of the use of a castout modulus that is both w-big and w-heavy applies to the use of a castout modulus that is both w-little and w-light with minor changes that are obvious to one of ordinary skill in the art.

Other moduli than w-big and w-heavy moduli as castout moduli would be used in other embodiments, and are therefore contemplated as falling within the scope of the claimed invention. And other moduli than w-little and w-light moduli as castout moduli would be used in other embodiments, and are therefore contemplated as falling within the scope of the claimed invention.

Other Embodiments

A factor in slowing some public-private key cryptosystem processes is their requirement for modular exponentiation of large numbers. Even though this description most thoroughly focuses on encryption/decryption embodiments, many other embodiments are contemplated. Examples of other embodiments—readily apparent to typical practitioners of this technical area—include (1) tomography/transforming data, (2) decryption/encryption, (3) keyless encryption, (4) combination transforming/detransforming, (5) random number generation/monte carlo, (5) simulation of real-life scenarios, etc. Those applications typically require heavy exponentiation and for that and other reasons would be particularly well adapted to application of the present invention.

In an embodiment, shotgun multiplication is used to facilitate high security log-ins that use high-degree-sparse polynomials. One example is Purdy. See G. B. Purdy, "A high security log-in procedure", Communications of the ACM, 17 (1974), 442-445.

In another embodiment, shotgun multiplication facilitates random number generation by staying shattered, generating new random strings indefinitely, with a clean-up unshatterer following to provide random numbers. One function example is LCPRN.

In a further embodiment, shotgun multiplication facilitates Monte Carlo.

In a yet another embodiment, shotgun multiplication facilitates simulation.

In a still further embodiment, shotgun multiplication facilitates speed acceleration of computer games.

In an embodiment, shotgun multiplication facilitates genetic algorithms.

In another embodiment, shotgun multiplication facilitates fractals.

In a further embodiment, shotgun multiplication facilitates morphing.

In a yet another embodiment, shotgun multiplication facilitates morphing particularly well for use in movie production.

In a still further embodiment, shotgun multiplication facilitates movie special effects, including random and nonrandom processes.

In other embodiments, shotgun multiplication facilitates secret sharing, some going into higher dimensional vector spaces, some over larger fields, and some involving ramp schemes.

In another embodiment, shotgun multiplication facilitates improved implementation of the invention disclosed in U.S. Pat. No. 5,485,474, "Scheme For Information Dispersal and Reconstruction," Rabin et al.

In further embodiments, shotgun multiplication facilitates extremely precise real calculations. Some of these are done as large-integer modular calculations, and some of these are done as large-modulus modular calculations. Error growth is minimized in some, and eliminated in others.

In yet other embodiments, shotgun multiplication facilitates transforms/retransforms. Examples of transforms/retransforms facilitated include Fourier, Laplace, Walsh, etc. Examples of classes facilitated include classical harmonic analysis, wavelet transforms, tomography, scattering, inverse scattering, sonar, and stealth technology.

Any element in a claim that does not explicitly state "means for" performing a specified function, or "step for" performing a specific function, is not to be interpreted as a "means" or "step" clause as specified in 35 U.S.C. §112, ¶6. In particular, the use of "step of" in the claims herein is not intended to invoke the provision of 35 U.S.C. §112, ¶6.

It should be apparent from the foregoing that an invention having significant advantages has been provided. While the invention is shown in only a few of its forms, it is not just limited to those forms but is susceptible to various changes and modifications without departing from the spirit thereof.

Appendix A—Glossary

This Glossary defines words as they are used throughout this application. This Glossary lists base words rather than word variations. But the meanings of word variations—such as "connecting," "connect," and "connected" for the base word "connection"—are also given meaning according to their logical relationship to the base word.

"=" means equality or congruence, depending on the context. This is clear to typical practitioners of this technical area.

"~"means approximately.

"algorithm" means a process for completing a task. An encryption algorithm is the process, typically with mathematical characteristics, to encrypt and decrypt messages.

"ARP" means Address Resolution Protocol. To map an IP address into a hardware address, a computing device uses the ARP protocol which broadcasts a request message containing an IP address, to which a target computing device replies with both the original IP address and the hardware address.

"Asymmetric encryption" means encryption used in a public-private key cryptosystem.

"Asymmetric key cipher" means a public-private key cryptography system.

"Authentication" means the process of verifying that a file or message has not been altered in route from the distributor to the recipient(s).

"Cipher" means a cryptographic algorithm used to encrypt an decrypt files and messages.

"Ciphertext" means the disguised (or encrypted) file or message.

"Computing device" means a device having at least one processor and at least one memory device, wherein the processor can process data that can be stored in the memory device before and/or after processing, or a group of devices having that capacity in combination. By this definition, examples of a computing device include computer personal computer, palm computing device, notebook computer, server, mainframe, network of computing devices with coordinated processing or storage, network of components functioning together as a computing device wherein any single component may not be a computing device in its own right, etc. As another example, components of a computing device may be connected across the Internet. Other examples of computing devices could include boards, chips, exponentiators, multipliers, etc.

"Connection" means any connection that is adapted to carry communication, whatever the supporting technology. Examples of connections include hard wire connections such as phone lines, T1 lines, DSL, fiber optic, Ethernet, twisted pair, etc. Other examples of connections include wireless connections such as those operating by electromagnetic waves, wireless optics (e.g., infrared), etc. Further examples are a logical connection between two processes on the same system, and a connection between two processes sharing a common memory space.

"Cryptanalysis" means the art of breaking cryptosystems. It also means the process of looking for errors or weaknesses in the implementation of an algorithm or of the algorithm itself.

"Cryptography" is the art of creating and using cryptosystems.

"Cryptosystem" means the entire process of using cryptography. This includes the actions of encrypting and decrypting a file or message. It also means authenticating the sender of an e-mail message.

"Decryption" means any process to convert ciphertext back into plaintext. Decrypting is synonymous to decoding.

"DES" means the Data Encryption Standard. It is a cipher developed by the United States government in the 1970s to be the official encryption algorithm of the United States.

"Digital signature" means systems that allow people and organizations to electronically certify such features as their identity, their ability to pay, or the authenticity of an electronic document.

"Encryption" means any process to convert plaintext into ciphertext. Encrypting is synonymous to encoding.

"FTP" means File Transfer Protocol. FTP enables transferring of text and binary files over TCP connections. FTP allows transferring files according to a strict mechanism of ownership and access restrictions. It is now one of the most commonly used protocols over the Internet.

"Hamming weight" means the number of "1" bits in the binary representation of a number.

"HTTP" means Hyper Text Transfer Protocol. It is a protocol used to transfer hypertext pages across the World Wide Web.

"IP" means Internet Protocol, and is the underlying protocol for the other Internet protocols. IP defines the means to identify and reach a target computer on the network. A unique number known as an IP address identifies each computing device in the IP world.

"IPSec" means Internet Protocol Security. It is a standard for security at the network or packet-processing layer of network communication. IPSec provides two choices of security service: Authentication Header (AH), which essentially allows authentication of the sender of data, and Encapsulating Security Payload (ESP), which supports both authentication of the sender and encryption of data. IPSec is a suite of protocols that protect client protocols of IP, such as TCP. IPSec describes mechanisms that provide data source authentication, data integrity, confidentiality and protection against replay attacks. IPSec provides transport mode and tunnel mode operation. Some embodiments provide only tunnel mode operation, and others offers a more complete IPSec implementation.

"iSCSI" is a software package that emulates SCSI protocols, but the connection method is via an IP network instead of a direct SCSI compatible cable. This is one example of IP-based storage.

"Key" means a collection of bits, usually stored in a file, which is used to encrypt or decrypt a message.

"Network protocol" means a standard designed to specify how computers interact and exchange messages. It usually specifies the format of the messages and how to handle errors. The following Internet protocols are examples of network protocols: ARP, FDi, HTTP, IP, NNTP PPP, SLIP, SMTP, SNMP, TCP, Telnet, and UDP.

"NNTP" means Network News Transfer Protocol. It is a protocol used to carry USENET postings between News clients and USENET servers.

"PGP" means Pretty Good Privacy. It is a public-private key cryptosystem that allows users to more easily integrate the use of encryption in their daily tasks, such as e-mail protection and authentication, and protecting files stored on a computer. PGP is available for free to individual home users.

"Plaintext" means the original message or file. After a file or message has been encrypted and then decrypted you should end up with the original file or message.

"PPP" means Point-To-Point protocol, and is a protocol for creating a TCP/IP connection over both synchronous and asynchronous systems. PPP provides connections for host-to-network or router-to-router. It also has a security mechanism. PPP is well known as a protocol for connections over regular telephone lines using modems on both ends. This protocol is widely used for connecting personal computers to the Internet.

"Private key" means the private key of a public-private key cryptosystem. This key is used to digitally sign outgoing messages and is used to decrypt incoming messages.

"Public key" means the public key of a public-private key cryptosystem. This key is used to confirm digital signatures on incoming messages or to encrypt a file or message so that only the holder of the private key can decrypt the file or message.

"Public key cryptosystem" means an asymmetric encryption algorithm in which it is infeasible to derive one key from the other.

"Public-private key cryptosystem" means a cryptosystem that uses two different keys to encrypt and decrypt messages and files. The two keys are mathematically related to each other, but deriving one key from the other is infeasible. One key is a public key and one key is a private key. The public key is usually distributed to other users, and the private key is usually kept secret.

"Ring arithmetic" means an arithmetic of mathematical structures in which addition, subtraction, multiplication, and their obvious consequences such as exponentiation, have the properties and interrelationships usually encountered in high school algebra.

"SCSI" is an intelligent protocol that enables data blocks to be read at high speed from or sent at high speed to storage devices such as disks or tape drives. Early implementations of SCSI used ribbon cable and industry standard logic levels.

"Security association" means a relationship between two or more entities that describes how the entities will utilize security services to communicate securely. This relationship is represented by a set of information that can be considered a contract between the entities. The information must be agreed upon and shared between all the entities. Security association is commonly abbreviated SA.

"Shotgun multiplication" means a process like that described in this application for performing fast computations by performing processing in mathematically independent units, taking advantage of more than one basis and precomputed operands, and accommodating iterative problems.

"SLIP" means Serial Line Internet Protocol, and is a point-to-point protocol to use over a serial connection, a predecessor of PPP. There is also an advanced version of this protocol known as CSLIP (compressed serial line internet protocol) that reduces overhead on a SLIP connection by sending just header information when possible, thus increasing packet throughput.

"SMTP" means Simple Mail Transfer Protocol, and is dedicated to sending e-mail messages originating on a local host to a remote server over a TCP connection. SMTP defines a set of rules that allows two programs to send and receive e-mail over the network. The protocol defines the data structure to deliver with information regarding the sender, the recipient(s) and the e-mail's body.

"SNMP" means Simple Network Management Protocol. It is a simple protocol that defines messages related to network management. Through the use of SNMP, network devices such as routers can be configured by any host on their network.

"SSL" means Secure Sockets Layer, and is a trademark of Netscape. It is a program layer created by Netscape for managing the security of message transmissions in a network. The concept is that the programming for keeping messages confidential is to be contained in a program layer between an application (such as a Web browser or HTTP) and the Internet's TCP/IP layers. The "sockets" part of the term refers to the sockets method of passing data back and forth between a client and a server program in a network or between program layers in the same computer.

"SSL/TLS" means compatible with SSL and with TLS.

"Symmetric key" means the key of a symmetric key cryptosystem. The symmetric key is used to encrypt a file or message and also to decrypt the file or message.

"Symmetric key cryptosystem" means a cryptosystem that uses one key to lock and unlock—encrypt and decrypt—messages and files. The sender must posses the key to encrypt a file or message, and the recipient(s) must possess the key to decrypt the file or message.

"TCP" means Transmission Control Protocol. Like UDP, TCP is a protocol that enables a computer to send data to a remote computer. But unlike UDP, TCP is reliable—packets are guaranteed to wind up at their target in the correct order.

"Telnet" is a terminal emulation protocol for use over TCP connections. It enables users to login to remote hosts and use their resources from the local host.

"TLS" means Transport Layer Security. It is the successor protocol to SSL, created by the Internet Engineering Task Force (IETF) for general communication authentication and encryption over TCP/IP networks. TLS version 1 is nearly identical with SSL version 3, providing data integrity and privacy on a communications link over the Internet. It allows client-server applications to communicate and is designed to prevent eavesdropping, message forgery, and interference.

"TOE" means TCP Offload Engine. TOE technology typically takes the server CPU out of I/O processing by shifting TCP/IP processing tasks to a network adapter or storage device. This leaves the CPU free to run its applications, so users get data faster.

"Triple DES" means a method of improving the strength of the DES algorithm by using it three times in sequence with different keys.

"UDP" means User Datagram Protocol. It is a simple protocol that transfers datagrams (packets of data) to a remote computer. UDP doesn't guarantee that packets will be received in the order sent or that they will arrive at all.

What is claimed is:

1. A method of encrypting data, comprising:
   choosing a modulus C for modular calculations, wherein C is a w-bit number, and wherein the modulus C is selected from the group consisting of (a) w-big and w-heavy, and (b) w-little and w-light; and
   using the modulus to encrypt data through a process involving a ring arithmetic function; wherein the modulus C is calculated by a process including
   (a) splitting a number $P<2^{2w}$ into 2 w-bit words $H_1$ and $L_1$;
   (b) calculating $S_1=L_1+(H_1 2^{x1})+(H_1 2^{x2})+\ldots+(H_1 2^{xk})+H_1$, wherein $(w-3)/2>x_1>x_2>\ldots>x_k>0$ and $k<<w$;
   (c) splitting $S_1$ into two w-bit words $H_2$ and $L_2$;
   (d) computing $S_2=L_2+(H_2 2^{x1})+(H_2 2^{x2})+\ldots(H_2 2^{x1})+H_2$;
   (e) computing $S_3=S_2+(2^{x1}+\ldots+2^{xk}+1)$;
   (f) determining the modulus C by comparing $S_3$ to 2w, wherein the modulus $C=S_2$ if $S_3<2^w$, and wherein the modulus $C=S_3-2^w$ if $S_3 \geq 2^w$;
   wherein the modulus C is a residue.

2. The method of claim 1, wherein the modulus C is of the form $2^w-L$, and wherein L is a low Hamming weight odd integer less than $2^{(w-1)/2}$.

3. The method of claim 1, wherein the modulus C is of the form $2^w+L$, and wherein the modulus C has a Hamming weight close to 1.

4. The method of claim 1, wherein the method of encrypting data comprises a method of cryptographic hashing.

5. The method of claim 1, wherein the modulus C is w-big and w-heavy.

6. The method of claim 1, wherein the modulus C is w-little and w-light.

7. The method of claim 1, wherein $C=2^w-2^{x1}-2^{x2}-\ldots-2^{xk}-1$, wherein $(w-3)/2>x_1>x_2>\ldots>x_k>0$, and wherein $k>>w$.

8. The method of claim 1, further comprising:
   choosing a first basis $(m_1, m_2, \ldots m_t)$ and a second basis $(m_{t+1}, m_{t+2}, \ldots m_{2t})$, wherein $m_1, \ldots m_{2t}$ are moduli;
   calculating a product $M=m_1 m_2 \ldots m_t$;
   calculating a product $W=m_{t+1} m_{t+2} \ldots m_{2t}$; and
   calculating a product $ABM^{-1}$ mod p for n-bit numbers A and B by (a) computing Q mod M in the first basis such that $AB+Qp=RM$ for some integral value R and for a number p which is prime relative to M and W; (b) converting Q to the second basis, Q mod W; and (c) computing R in the second basis, R mod W, wherein $R=(AB+Qp) M^{-1}$ mod W and R mod $p=ABM^{-1}$ mod p.

9. The method of claim 8 wherein, for i=1 to 2t, $2^{k-1} \leq m_i \leq 2^k$, and wherein $m_1, \ldots, m_{2t}$ are pairwise mutually prime.

10. The method of claim 9, wherein $t \geq (n+1)/k$, where n is the bit length of the numbers being multiplied.

11. The method of claim 1, further comprising:
    performing a ring arithmetic function on numbers, including (a) using a residue number multiplication process, (b) converting to a first basis using a mixed radix system, and (c) converting to a second basis using a mixed radix system.

12. A method of encrypting data, comprising:
choosing a modulus C for modular calculations, wherein C is a w-bit number, and wherein the modulus C is selected from the group consisting of (a) w-big and w-heavy, and (b) w-little and w-light; and
using the modulus to encrypt data through a process involving a ring arithmetic function; wherein the method further comprises
choosing a first basis $(m_1, m_2, \ldots m_t)$ and a second basis $(m_{t+1}, m_{t+2}, \ldots m_{2t})$, wherein $m_1, \ldots, m_{2t}$ are moduli,
calculating a product $M = m_1 m_2 \ldots m_t$,
calculating a product $W = m_{t+1} m_{t+2} \ldots m_{2t}$, and
calculating a product $ABM^{-1}$ mod p for n-bit numbers A and B by (a) computing Q mod M in the first basis such that $AB + Qp = RM$ for some integral value R and for a number p which is prime relative to M and W; (b) converting Q to the second basis, Q mod W; and (c) computing R in the second basis, R mod W, wherein $R = (AB + Qp) M^{-1}$ mod W and R mod p = $ABM^{-1}$ mod p.

13. The method of claim 12, further comprising:
performing a ring arithmetic function on numbers, including (a) using a residue number multiplication process, (b) converting to a first basis using a mixed radix system, and (c) converting to a second basis using a mixed radix system.

14. The method of claim 12, wherein the modulus C is of the form $2^w - L$, and wherein L is a low Hamming weight odd integer less than $2^{(w-1)/2}$.

15. The method of claim 12, wherein the modulus C is of the form $2^w + L$, and wherein the modulus C has a Hamming weight close to 1.

16. The method of claim 12, wherein the method of encrypting data comprises a method of cryptographic hashing.

17. The method of claim 12, wherein the modulus C is w-big and w-heavy.

18. The method of claim 12, wherein the modulus C is w-little and w-light.

19. The method of claim 12, wherein $C = 2^w - 2^{x1} - 2^{x2} - \ldots - 2^{xk} - 1$, wherein $(w-3)/2 > x_1 > x_2 > \ldots > x_k > 0$, and wherein $k \gg w$.

20. The method of claim 12 wherein, for i=1 to 2t, $2^{k-1} \leq m_i \leq 2^k$, and wherein $m_1, \ldots, m_{2t}$ are pairwise mutually prime.

21. The method of claim 20, wherein $t \geq (n+1)/k$, where n is the bit length of the numbers being multiplied.

22. The method of claim 21, wherein p is an n-bit number, and wherein p is a prime number.

23. The method of claim 20, further comprising converting R to the first basis, R mod M.

24. The method of claim 12, wherein the step of calculating a product $ABM^{-1}$ mod p is performed iteratively and includes at least first and second subsequent iterations, and wherein the value of R calculated in the first iteration is utilized as the input value of R in the second iteration.

25. The method of claim 12, wherein the data is encrypted using asymmetric encryption.

26. The method of claim 12, wherein the data is encrypted using symmetric encryption.

27. The method of claim 12, further comprising:
performing a ring arithmetic function on numbers, including (a) using a residue number multiplication process, (b) converting to a first basis using a mixed radix system, and (c) converting to a second basis using a mixed radix system.

* * * * *